United States Patent
Cassayre et al.

(10) Patent No.: US 8,586,593 B2
(45) Date of Patent: Nov. 19, 2013

(54) INSECTICIDAL COMPOUNDS

(75) Inventors: Jerome Yves Cassayre, Stein (CH); Thomas Pitterna, Stein (CH); Camilla Corsi, Stein (CH); Peter Maienfisch, Stein (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 107 days.

(21) Appl. No.: 13/382,688

(22) PCT Filed: Jun. 7, 2010

(86) PCT No.: PCT/EP2010/057907
§ 371 (c)(1),
(2), (4) Date: Jan. 6, 2012

(87) PCT Pub. No.: WO2011/003684
PCT Pub. Date: Jan. 13, 2011

(65) Prior Publication Data
US 2012/0115884 A1    May 10, 2012

(30) Foreign Application Priority Data
Jul. 6, 2009 (EP) .................... 09164662

(51) Int. Cl.
*C07D 401/14* (2006.01)
*A01N 43/54* (2006.01)
(52) U.S. Cl.
USPC .......................... 514/256; 544/333
(58) Field of Classification Search
USPC .......................... 544/333; 514/256
See application file for complete search history.

(56) References Cited

U.S. PATENT DOCUMENTS

2011/0136866 A1* 6/2011 Pitterna et al. ............... 514/318

FOREIGN PATENT DOCUMENTS

WO    2006003494 A2    1/2006

OTHER PUBLICATIONS

Mollusca, From Wikipedia, the free encyclopedia (2013).*
Nematode, From Wikipedia, the free encyclopedia (2013).*
Acari, From Wikipedia, the free encyclopedia (2013).*

* cited by examiner

*Primary Examiner* — Deepak Rao
(74) *Attorney, Agent, or Firm* — Brian D. McAlhaney

(57) ABSTRACT

A compound of formula (I) wherein A, p, $R^1$, $R^3$, $R^4$, $R^5$, and $R^8$ are as defined in claim 1. Furthermore, the present invention relates to intermediates used to prepare compounds of formula (I), to methods of using them to combat and control insect, acarine, nematode and mollusc pests and to insecticidal, acaricidal, nematicidal and molluscicidal compositions comprising them.

8 Claims, No Drawings

INSECTICIDAL COMPOUNDS

This application is a 371 of International Application No. PCT/EP2010/057907 filed Jun. 7, 2010, which claims priority to EP 09164662.0 filed Jul. 6, 2009, the contents of which are incorporated herein by reference.

The present invention relates to certain piperidine derivatives, to processes for preparing them, to insecticidal, acaricidal, molluscicidal and nematicidal compositions comprising them and to methods of using them to combat and control insect, acarine, mollusc and nematode pests.

Piperidine derivatives with insecticidal properties are disclosed, for example, in WO 2006/003494.

It has now surprisingly been found that certain piperidines have enhanced insecticidal properties.

The present invention therefore provides a compound of formula (I):

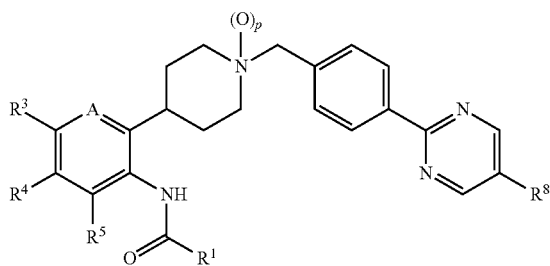

wherein
A is $CR^2$ or N;
p is 0 or 1;
$R^1$ is pyrid-4-yl optionally substituted by one or two substituents each independently selected from halogen, $C_1$-$C_3$alkyl, $C_1$-$C_3$haloalkyl, or $C_1$-$C_3$alkoxy;
$R^2$ is hydrogen, halogen, $C_1$-$C_3$haloalkyl or $C_1$-$C_3$haloalkoxy;
$R^3$ and $R^4$ are independently hydrogen, halogen, cyano, $C_1$-$C_8$alkyl, $C_1$-$C_8$haloalkyl, $C_2$-$C_8$alkenyl, $C_2$-$C_8$haloalkenyl, $C_3$-$C_8$cycloalkyl, $C_3$-$C_8$halocycloalkyl, $C_1$-$C_8$alkoxy, $C_1$-$C_8$haloalkoxy, $C_1$-$C_8$alkylthio or $C_1$-$C_8$haloalkylthio;
$R^5$ is hydrogen or halogen; and
$R^8$ is hydrogen, halogen, cyano, $C_1$-$C_8$alkyl, $C_1$-$C_8$haloalkyl, $C_3$-$C_8$cycloalkyl, $C_2$-$C_8$alkenyl, $C_2$-$C_8$haloalkenyl, $C_2$-$C_8$alkynyl, $C_1$-$C_8$alkoxy or $C_1$-$C_8$haloalkoxy; or a salt thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy or alkylthio) is a straight or branched chain and is, for example, methyl, ethyl, n-propyl, iso-propyl, n-butyl, sec-butyl, iso-butyl or tert-butyl. The alkyl groups are preferably $C_1$-$C_6$, more preferably $C_1$-$C_4$ and most preferably $C_1$-$C_3$ alkyl groups.

Alkenyl and alkynyl moieties can be in the form of straight or branched chains, and the alkenyl moieties, where appropriate, can be of either the (E)- or (Z)-configuration. Examples are vinyl, allyl and propargyl. The alkenyl and alkynyl groups are preferably $C_2$-$C_6$, more preferably $C_2$-$C_4$ and most preferably $C_2$-$C_3$ alkenyl or alkynyl groups.

Halogen is fluorine, chlorine, bromine or iodine.

Haloalkyl groups (either alone or as part of a larger group, such as haloalkoxy or haloalkylthio) are alkyl groups which are substituted with one or more of the same or different halogen atoms and are, for example, —$CF_3$, —$CF_2Cl$, —$CH_2CF_3$ or —$CH_2CHF_2$.

Haloalkenyl are alkenyl groups which are substituted with one or more of the same or different halogen atoms and are, for example, —CH=$CF_2$ or —CCl=CClF.

Haloalkenyl groups are alkenyl groups, respectively, which are substituted with one or more of the same or different halogen atoms and are, for example, —CH=$CF_2$ or —CCl=CClF.

Cycloalkyl groups can be in mono- or bi-cyclic form and may optionally be substituted by one or more methyl groups. The cycloalkyl groups preferably contain 3 to 8 carbon atoms, more preferably 3 to 6 carbon atoms. Examples of monocyclic cycloalkyl groups are cyclopropyl, 1-methyl-cyclopropyl, 2-methyl-cyclopropyl, cyclobutyl, cyclopentyl and cyclohexyl.

Halocycloalkyl groups are cycloalkyl groups which are substituted with one or more of the same of different halogen atoms and may optionally be substituted by one or more methyl groups. Examples of monocyclic halocycloalkyl groups are 2,2-dichloro-cyclopropyl, 2,2-dichloro-1-methyl-cyclopropyl and 2-chloro-4-fluoro-cyclohexyl.

Preferred groups and values for $R^1$, $R^2$, $R^3$, $R^4$, $R^5$ and $R^8$ in any combination thereof are set out below.

Preferably $R^1$ is pyrid-4-yl optionally substituted by one or two substituents each independently selected from fluoro, chloro, bromo, methyl, difluoromethyl, chloro-difluoromethyl, trifluoromethyl or methoxy; more preferably $R^1$ is pyrid-4-yl optionally substituted by one or two substituents each independently selected from fluoro, chloro or methyl; most preferably $R^1$ is pyrid-4-yl substituted by one or two substituents each independently selected from fluoro or chloro. It is preferred that one substituent occupies the 2-position of the pyrid-4-yl ring and that optionally a second substituent occupies the 5- or 6-position of the pyrid-4-yl ring. Examples of most preferred $R^1$ groups include 2-fluoro-pyrid-4-yl, 2-chloro-pyrid-4-yl, 2,5-dichloro-pyrid-4-yl, and 2,6-dichloro-pyrid-4-yl.

Preferably $R^2$ is hydrogen or halogen.
More preferably $R^2$ is hydrogen, fluoro or chloro.
Even more preferably $R^2$ is hydrogen or fluoro.
Most preferably $R^2$ is hydrogen.
Preferably $R^3$ is hydrogen, halogen, cyano, $C_1$-$C_6$alkyl, $C_1$-$C_6$haloalkyl, $C_2$-$C_6$alkenyl, $C_3$-$C_6$cycloalkyl, $C_1$-$C_6$alkoxy, $C_1$-$C_6$haloalkoxy, $C_1$-$C_6$alkylthio or $C_1$-$C_6$haloalkylthio.

More preferably $R^3$ is hydrogen, fluoro, chloro, bromo, cyano, methyl, iso-propyl, fluoromethyl, difluoromethyl, trifluoromethyl, heptafluoro-iso-propyl, vinyl, cyclopropyl, methoxy, ethoxy, difluoromethoxy, trifluoromethoxy, 2,2,2-trifluoroethoxy or trifluoromethylthio.

Even more preferably $R^3$ is hydrogen, fluoro, chloro, bromo, difluoromethyl, trifluoromethyl, heptafluoro-iso-propyl, vinyl, cyclopropyl, methoxy, difluoromethoxy, trifluoromethoxy or 2,2,2-trifluoroethoxy.

Yet even more preferably $R^3$ is hydrogen, fluoro, chloro, bromo, trifluoromethyl, cyclopropyl or trifluoromethoxy.

Most preferably $R^3$ is trifluoromethyl.

Preferably $R^4$ is hydrogen, halogen, cyano, $C_1$-$C_6$alkyl, $C_1$-$C_6$haloalkyl, $C_2$-$C_6$alkenyl, $C_3$-$C_6$cycloalkyl, $C_1$-$C_6$alkoxy, $C_1$-$C_6$haloalkoxy, $C_1$-$C_6$alkylthio or $C_1$-$C_6$haloalkylthio.

More preferably $R^4$ is hydrogen, fluoro, chloro, bromo, methyl, iso-propyl, fluoromethyl, difluoromethyl, trifluoromethyl, heptafluoro-iso-propyl, vinyl, cyclopropyl, methoxy, ethoxy, difluoromethoxy, trifluoromethoxy or 2,2,2-trifluoroethoxy.

Even more preferably $R^4$ is hydrogen, fluoro, chloro, methyl or trifluoromethyl.

Most preferably $R^4$ is hydrogen.

Preferably $R^5$ is hydrogen, fluoro, chloro or bromo.

More preferably $R^5$ is hydrogen or fluoro.

Most preferably $R^5$ is hydrogen.

Preferably $R^8$ is hydrogen, halogen, cyano, $C_1$-$C_6$alkyl, $C_1$-$C_6$haloalkyl, $C_3$-$C_6$cycloalkyl, $C_2$-$C_6$alkenyl, $C_2$-$C_6$haloalkenyl, $C_2$-$C_6$alkynyl, $C_1$-$C_6$alkoxy or $C_1$-$C_6$haloalkoxy.

More preferably $R^8$ is hydrogen, fluoro, chloro, bromo, cyano, methyl, trifluoromethyl, cyclopropyl, ethynyl, methoxy or trifluoromethoxy.

Even more preferably $R^8$ is hydrogen, fluoro, chloro, bromo, trifluoromethyl or trifluoromethoxy.

Yet even more preferably $R^8$ is fluoro or chloro.

Most preferably $R^8$ is chloro.

One preferred embodiment are compounds of formula (Ia) wherein $R^1$, $R^3$, $R^4$, $R^5$ and $R^8$ are as defined for a compound of formula (I), A is $CR^2$, and p is 0. The preferences for $R^1$, $R^2$, $R^3$, $R^4$, $R^5$ and $R^8$ are the same as set out for a compound of formula (I).

Another preferred embodiment are compounds of formula (Ib) wherein $R^1$, $R^3$, $R^4$, $R^5$ and $R^8$ are as defined for a compound of formula (I), A is N, and p is 0. The preferences for $R^1$, $R^3$, $R^4$, $R^5$ and $R^8$ are the same as set out for a compound of formula (I).

Yet another preferred embodiment are compounds of formula (Ic) wherein $R^1$, $R^3$, $R^4$, $R^5$ and $R^8$ are as defined for a compound of formula (I), A is $CR^2$, and p is 1. The preferences for $R^1$, $R^2$, $R^3$, $R^4$, $R^5$ and $R^8$ are the same as set out for a compound of formula (I).

A preferred embodiment are compounds of formula (Id) wherein $R^1$, $R^3$, $R^4$, $R^5$ and $R^8$ are as defined for a compound of formula (I), A is N, and p is 1. The preferences for $R^1$, $R^3$, $R^4$, $R^5$ and $R^8$ are the same as set out for a compound of formula (I).

A further preferred embodiment are salts of formula (Ie) wherein $R^1$, $R^3$, $R^4$, $R^5$ and $R^8$ are as defined for a compound of formula (I), A is $CR^2$, p is 0, and the salt is formed by treatment with an acid selected from hydrochloric acid, acetic acid, 2-chlorobenzoic acid, 2-hydroxy-benzoic acid, ethane sulfonic acid, 3-hydroxypropane-1-sulfonic acid, methane sulfonic acid, (4-methylphenyl)sulfonic acid (Toluene-4-sulfonic acid), 3-phenoxy-propionic acid, phosphoric acid, 2,3,4,5-Tetrahydroxy-6-oxo-hexanoic acid, tridecanoic acid, trifluoroacetic acid, glucoronic acid, and salicylic acid. The preferences for $R^1$, $R^2$, $R^3$, $R^4$, $R^5$ and $R^8$ are the same as set out for a compound of formula (I). The acid is preferably acetic acid or hydrochloric acid.

A preferred embodiment are salts of formula (If) wherein $R^1$, $R^3$, $R^4$, $R^5$ and $R^8$ are as defined for a compound of formula (I), A is N, p is 0, and the salt is formed by treatment with an acid as defined for a compound of formula (Ie). The preferences for $R^1$, $R^3$, $R^4$, $R^5$ and $R^8$ are the same as set out for a compound of formula (I). The acid is preferably acetic acid or hydrochloric acid. Certain intermediates are novel and as such form a further aspect of the invention. One such group of intermediates are compounds of formula (II)

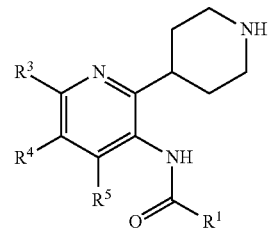

(II)

wherein $R^1$, $R^3$, $R^4$ and $R^5$ are defined as for a compound of formula (I). The preferences for $R^1$, $R^3$, $R^4$ and $R^5$ are the same as set out for a compound of formula (I).

Another group of intermediates are compounds of formula (III)

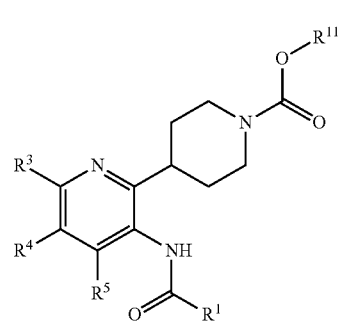

(III)

wherein $R^1$, $R^3$, $R^4$ and $R^5$ are defined as for a compound of formula (I); and $R^{11}$ is $C_1$-$C_6$alkyl, such as tert-butyl, $C_2$-$C_6$alkenyl, such as allyl, or benzyl optionally substituted with one to three substituents independently selected from halogen, $C_1$-$C_6$alkyl, $C_1$-$C_6$haloalkyl, $C_1$-$C_6$alkoxy or $C_1$-$C_6$haloalkoxy. The preferences for $R^1$, $R^3$, $R^4$ and $R^5$ are the same as set out for a compound of formula (I). $R^{11}$ is preferably tert-butyl.

Another group of intermediates are compounds of formula (IV)

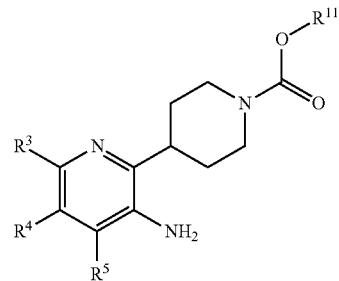

(IV)

wherein $R^3$, $R^4$ and $R^5$ are defined as for a compound of formula (I), or $R^3$ and $R^5$ are hydrogen and $R^4$ is fluoro, chloro or trifluoromethyl; and $R^{11}$ is defined as for a compound of formula (III). The preferences for $R^3$, $R^4$ and $R^5$ are the same as set out for a compound of formula (I). The preference for $R^{11}$ is the same as set out for a compound of formula (III).

Another group of intermediates are compounds of formula (V)

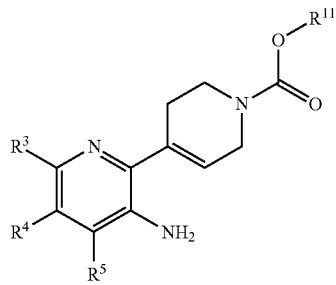

wherein $R^3$, $R^4$ and $R^5$ are defined as for a compound of formula (I), or $R^3$ and $R^5$ are hydrogen and $R^4$ is fluoro, chloro or trifluoromethyl; and $R^{11}$ is defined as for a compound of formula (III). The preferences for $R^3$, $R^4$ and $R^5$ are the same as set out for a compound of formula (I). The preference for $R^{11}$ is the same as set out for a compound of formula (III).

Another group of intermediates are compounds of formula (VI)

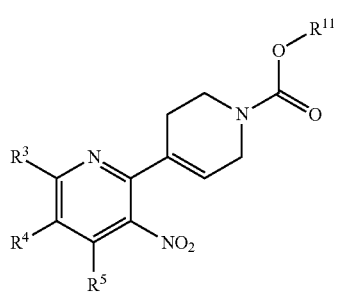

wherein $R^3$, $R^4$ and $R^5$ are defined as for a compound of formula (I); and $R^{11}$ is as defined for a compound of formula (III). The preferences for $R^3$, $R^4$ and $R^5$ are the same as set out for a compound of formula (I). The preference for $R^{11}$ is the same as set out for a compound of formula (III).

Another group of intermediates are compounds of formula (3)

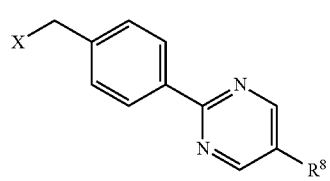

wherein $R^8$ is defined as for a compound of formula (I); and X is chloro or bromo. The preference for $R^8$ is the same as set out for a compound of formula (I). The preference for X is chloro.

Another group of intermediates are compounds of formula (4)

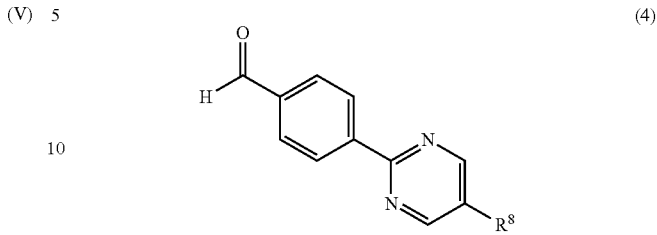

wherein $R^8$ is defined as for a compound of formula (I). The preference for $R^8$ is the same as set out for a compound of formula (I).

The compounds of the invention may be made by a variety of methods as mentioned in WO 2006/003494. For example, compounds of formula (I) may be prepared according to Schemes 1, 2 and 3.

Thus a compound of formula (1) wherein A, $R^1$, $R^3$, $R^4$, $R^5$ and $R^8$ are as defined for a compound of formula (I), may be obtained from a compound of formula (2) wherein A, $R^1$, $R^3$, $R^4$ and $R^5$ are as defined for a compound of formula (I), by reaction with a compound of formula (3) wherein $R^8$ is as defined for a compound of formula (I) and X is a leaving group, such as a halide (e.g. chloride, bromide or iodide) or a sulfonate (e.g. mesylate or tosylate), in the presence of a base, such as a tertiary amine (e.g. diisopropylethylamine or triethylamine), in an organic solvent, such as dichloromethane, acetonitrile or N,N-dimethylformamide, at a temperature of between 0° C. and 100° C., typically at ambient temperature, as shown in Scheme 1.

Scheme 1

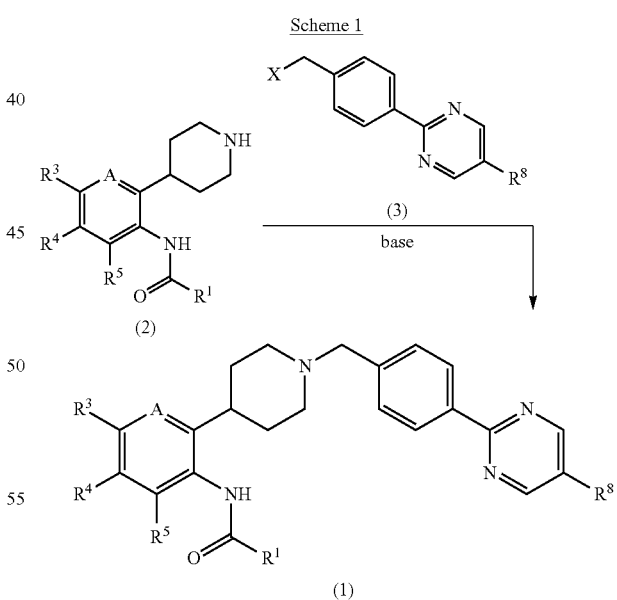

Alternatively, a compound of formula (1) as defined above, may be obtained from a compound of formula (2) as defined above, by reaction with an aldehyde of formula (4) wherein $R^8$ is as defined for a compound of formula (I) in the presence of a reducing agent, such as sodium (triacetoxy)borohydride, sodium cyanoborohydride or borane or the like, in an organic solvent, such as tetrahydrofuran, methanol or ethanol, at a temperature of between 0° C. and 100° C., typically at ambient temperature, as shown in Scheme 2.

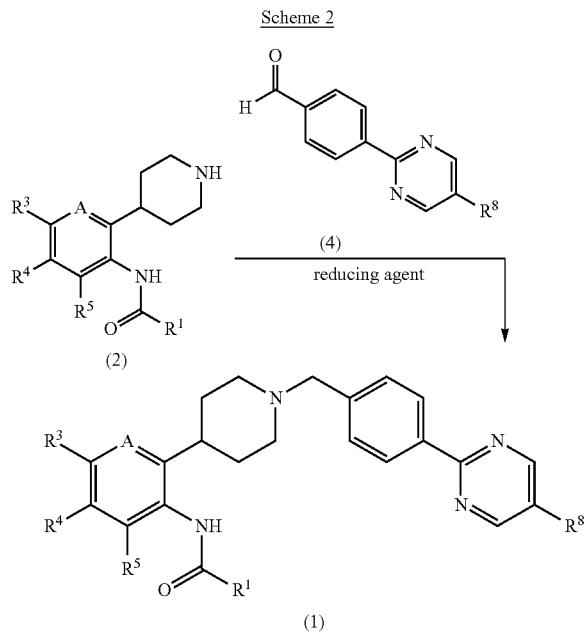

Scheme 2

(2)

reducing agent (1)

Compounds of formula (2) can be prepared as described in WO 2006/003494. Examples of these methods can be found in the preparation examples.

Compounds of formula (3) and (4) are either known compounds or may be prepared by methods known to a person skilled in the art. Examples of these methods can be found in the preparation examples.

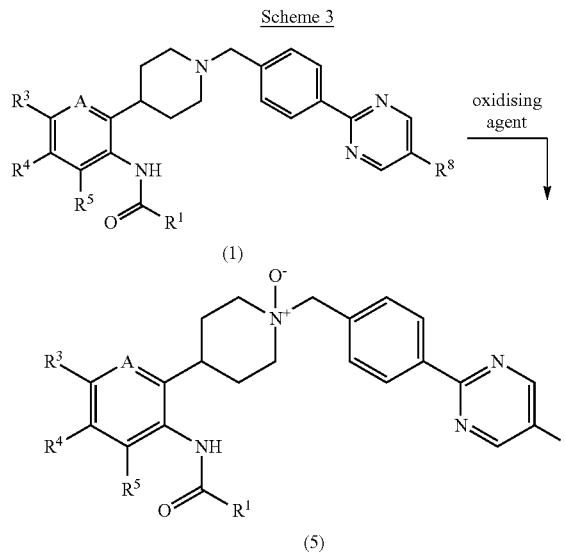

Scheme 3

(1)

oxidising agent (5)

N-oxides of formula (5) may be prepared by oxidation of a compound of formula (1) with an oxidising agent, such as hydrogen peroxide or 3-chloroperoxybenzoic acid, in an organic solvent, such as dichloromethane, ethanol, methanol or water or mixtures of solvents, at a temperature of between −78° C. and 100° C., typically at ambient temperature, as shown in Scheme 3.

The compound of formula (I) have enhanced pesticidal properties. For example, the compounds may have increased insecticidal activity and/or improved photostability.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus,* and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest. The compounds of formula (I) are preferably used against insects, acarines or nematodes.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

In a still further aspect the invention provides a method of combating and controlling pests at a locus which comprises treating the pests or the locus of the pests with an insecticidally, acaricidally, nematicidally or molluscicidally effective amount of a composition comprising a compound of formula (I). The compounds of formula (I) are preferably used against insects, acarines or nematodes.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium hydrogencarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at ambient temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures suitably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example etofenprox), natural pyrethrin, tetramethrin, s-bioallethrin, fenfluthrin, prallethrin or 5-benzyl-3-furylmethyl-(E)-(1R,3S)- 2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, chloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, or spinosad, spinetoram or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds such as imidacloprid, thiacloprid, acetamiprid, clothianidin, nitenpyram, dinotefuran or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;

q) Pymetrozine or pyrifluquinazon;

r) Spirotetramat, spirodiclofen or spiromesifen;

s) Flubendiamide, chloranthraliniprole, or cyanthraniliprole;

t) Cyenopyrafen or cyflumetofen; or u) Sulfoxaflor.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5-dimethyl-2-trimethylsilylthiophene-3-carboxamide (MON65500), N-(1-cyano-1,2-dimethylpropyl)-2-(2,4-dichlorophenoxy) propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)—N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples:

LCMS. Spectra were recorded on a ZMD (Micromass, Manchester UK) or a ZQ (Waters Corp. Milford, Mass., USA) mass spectrometer equipped with an electrospray source (ESI; source temperature 80 to 100° C.; desolvation temperature 200 to 250° C.; cone voltage 30 V; cone gas flow 50 l/hr, desolvation gas flow 400 to 600 l/hr, mass range: 150 to 1000 Da) and an Agilent 1100 HPLC column: Gemini C18, 3 μm particle size, 110 Angstrom, 30×3 mm (Phenomenex, Torrance, Calif., USA); column temperature: 60° C.; flow rate 1.7 ml/min; eluent A: H$_2$O/HCOOH 100:0.05; eluent B: MeCN/MeOH/HCOOH 80:20:0.04; gradient: 0 min 5% B; 2-2.8 min 100% B; 2.9-3 min 5% B; UV-detection: 200-500 nm, resolution 2 nm. The flow was split post column prior to MS analysis. RT stands for retention time.

EXAMPLE 1

This example illustrates the preparation of 2-chloro-N-(2-{1-[4-(5-chloro-pyrimidin-2-yl)-benzyl]-piperidin-4-yl}-4-trifluoromethyl-phenyl)-isonicotinamide (Compound A1 of Table A)

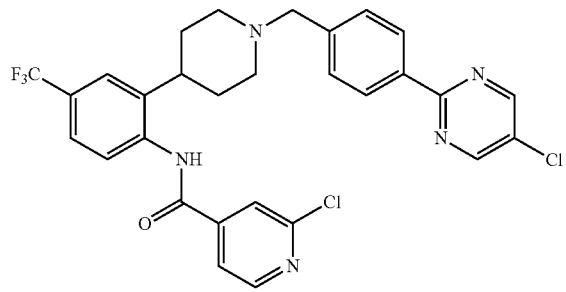 [SMILES: O=C(Nc1ccc(C(F)(F)F)cc1C1CCN(Cc2ccc(-c3ncc(Cl)cn3)cc2)CC1)c1ccnc(Cl)c1]

Step A:

A 4.5 L reactor was charged with 2-bromo-4-trifluoromethyl aniline (100 g), 4-(4,4,5,5-tetramethyl-[1,3,2]dioxaborolan-2-yl)-3,6-dihydro-2H-pyridine-1-carboxylic acid tert-butyl ester (124 g, prepared as described in WO 2006/003494), 1,4-dioxane (2500 ml) and the solution was degassed for 30 minutes with argon. Dichloro-bis(triphenylphosphine)-palladium (5.6 g) was added and the resulting solution was stirred for 30 minutes at ambient temperature under an argon atmosphere. A degassed solution of sodium carbonate (127 g) in water (1200 ml) was added and the mixture was stirred at 60° C. for 3 hours. The mixture was cooled to ambient temperature and extracted with ethyl acetate (3×300 ml). The combined organic layers were washed with water (3×400 ml), brine then dried over sodium sulfate and concentrated in vacuo. The residue was dissolved in heptane (200 ml) and cooled to −70° C. and then allowed to warm to 0° C. The solid was collected by filtration and rinsed with cold heptane to afford 4-(2-amino-5-trifluoromethyl-phenyl)-piperidine-1-carboxylic acid tert-butyl ester (128 g) as a brown solid. MS (ES+) 214/215; 243/244 (MH+-BOC); 287/288; 343 (MH+); 1H NMR (400 MHz, CDCl$_3$) 1.5 (s, 9H), 2.4 (m, 2H), 3.65 (t, 2H), 4.05 (m, 2H), 5.8 (m, 1H), 6.7 (d, 1H), 7.2 (d, 1H), 7.3 (dd, 1H).

Step B:

The compound obtained in Step A (152 g) was dissolved in ethanol (2100 ml) and after degassing, palladium on charcoal (10% by weight) (100 mg) was added. The reaction mixture was stirred at ambient temperature under a hydrogen atmosphere for 30 hours. Filtration on Celite® furnished a dark solid which was dissolved in diethyl ether (1000 ml). Filtration over Hyflo® and evaporation of the solvent gave a yellow residue, which was precipitated from petroleum ether (1000 ml) to afford 4-(2-amino-5-trifluoromethyl-phenyl)-piperidine-1-carboxylic acid tert-butyl ester (125 g) as a white solid. M.p. 120° C. MS (ES+) 330/331 (MH+-isobutene+ CH$_3$CN); 1H NMR (400 MHz, CDCl$_3$) 1.5 (s, 9H), 1.6 (m, 2H), 1.85 (m, 2H), 2.6 (m, 1H), 2.8 (m, 2H), 3.95 (br s, 2H), 4.3 8 m, 2H), 6.7 (d, 1H), 7.3 (d, 2H).

Step C:

To a suspension of 2-chloro-isonicotinic acid (56 g) in toluene (1500 ml) and N,N-dimethylformamide (0.5 ml) under a nitrogen atmosphere at ambient temperature, was added dropwise thionyl chloride (81 ml) and the mixture was stirred at 60° C. until the all the solids dissolved (3 hours). The solution was concentrated in vacuo and the residue was dissolved in tetrahydrofuran (300 ml). This solution was added dropwise into a solution of the product obtained in Step B (103 g) in tetrahydrofuran (3000 ml) and N,N-diisopropyl-ethylamine (155 ml) at ambient temperature. The reaction mixture was stirred for 3 hours at ambient temperature, quenched by addition of aqueous sodium hydrogen carbonate (saturated) (1000 ml) and extracted with ethyl acetate (3×500 ml). The combined organic extracts were washed with water (3×500 ml) then brine (200 ml), dried over sodium sulfate and concentrated in vacuo. The residue was triturated with diethyl ether, the solid isolated by filtration and dried under high vacuum to afford 4-{2-[(2-chloro-pyridine-4-carbonyl)-amino]-5-trifluoromethyl-phenyl}-piperidine-1-carboxylic acid tert-butyl ester (143 g) as a white powder. MS (ES+) 384/386 (MH⁺-BOC), 428/430 (MH⁺-isobutene), 484/486 (MH⁺); 1H NMR (400 MHz, CDCl$_3$) 1.5 (s, 9H), 1.7 (m, 2H), 1.85 (m, 2H), 2.8 (m, 3H), 4.3 (m, 2H), 7.6 (m, 2H), 7.65 (d, 1H), 7.70 (d, 1H), 7.80 (s, 1H), 8.0 (s, 1H), 8.6 (d, 1H).

Step D:

A solution of the product obtained in Step C (140 g) in dichloromethane (1500 ml) was treated with trifluoroacetic acid (220 ml) and the reaction mixture was stirred at ambient temperature under a nitrogen atmosphere for 1 hour. Then the reaction mixture was concentrated in vacuo to give a residue, which was precipitated from diethyl ether to afford 2-chloro-N-(2-piperidin-4-yl-4-trifluoromethyl-phenyl)-isonicotinamide as its trifluoroacetate salt (white solid, 144 g). M.p. 248° C. MS (ES+) 384/386 (MH+). The free base was obtained by first neutralizing with aqueous sodium hydroxide (1N) to pH 9 and then extracting with ethyl acetate. Removal of the solvent yielded a yellow solid. M.p. 166° C.

Step E:

The product obtained in Step D (free base, 38 g) was mixed with 4-(5-chloro-pyrimidin-2-yl)-benzaldehyde (Preparation 1, 22 g) and dissolved in tetrahydrofuran (500 ml). The solution was stirred under an argon atmosphere and treated with sodium cyanoborohydride (33 g). The resulting mixture was stirred for 16 hours at ambient temperature, quenched by addition of water and the mixture extracted with ethyl acetate. The organic layer was dried over sodium sulfate and concentrated in vacuo to give a beige solid, 2-chloro-N-(2-{1-[4-(5-chloro-pyrimidin-2-yl)-benzyl]-piperidin-4-yl}-4-trifluoromethyl-phenyl)-isonicotinamide acetate (Compound E1 of Table E). This salt was dissolved in ethyl acetate, then neutralized with aqueous sodium hydroxide (2N), and washed with water and brine. The combined organic layers were dried over sodium sulfate and the solvent removed under reduced pressure to afford the title compound as a white solid. M.p. 202-203° C. MS (ES+) 586/588 (MH⁺); 1H NMR (400 MHz, DMSO) 1.7 (m, 4H), 2.0 (m, 2H), 2.9 (m, 3H), 3.3 (s, 2H), 7.45 (d, 2H), 7.55 (d, 1H), 7.60 (d, 1H), 7.70 (s, 1H), 7.90 (d, 1H), 8.0 (s, 1H), 8.3 (d, 2H), 8.65 (d, 1H), 9.0 (s, 2H).

EXAMPLE 2

This example illustrates the preparation of 2-chloro-N-(2-{1-[4-(5-fluoro-pyrimidin-2-yl)-benzyl]-piperidin-4-yl}-4-trifluoromethyl-phenyl)-isonicotinamide (Compound A2 of Table A)

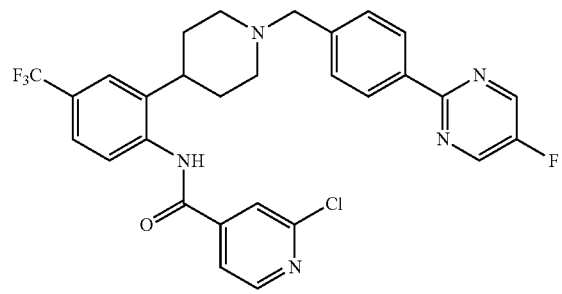 [SMILES: O=C(Nc1ccc(C(F)(F)F)cc1C1CCN(Cc2ccc(-c3ncc(F)cn3)cc2)CC1)c1ccnc(Cl)c1]

The title compound was prepared according to a procedure similar to those described in Example 1 using 4-(5-fluoro-pyrimidin-2-yl)-benzaldehyde (Preparation 2) in Step E. M.p. 89-90° C. The acetate salt (Compound E2 of Table E) was also isolated.

EXAMPLE 3

This example illustrates the preparation of 2-chloro-N-(2-{1-[4-(5-chloro-pyrimidin-2-yl)-benzyl]-piperidin-4-yl}-4-fluoro-phenyl)-isonicotinamide (Compound A10 of Table A).

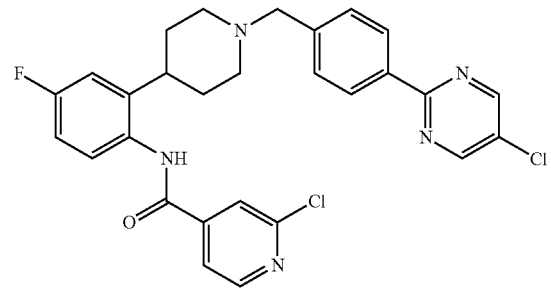 [SMILES: O=C(Nc1ccc(F)cc1C1CCN(Cc2ccc(-c3ncc(Cl)cn3)cc2)CC1)c1ccnc(Cl)c1]

A mixture of 2-chloro-N-(4-fluoro-2-piperidin-4-yl-phenyl)-isonicotinamide (333 mg) (prepared according to procedures analogous to those described in WO 2006/003494) was treated with 4-(5-chloro-pyrimidin-2-yl)-benzaldehyde (Preparation 1, 218 mg) and sodium cyanoborohydride (316 mg) in tetrahydrofuran (50 ml) as described in Example 1, Step E to afford the title compound (200 mg) as a white solid. M.p. 176° C. MS (ES+) 536/538 (MH+), 308/309 (M-isoprene); 1H NMR (400 MHz, MeOD) 1.7 (m, 4H), 2.1 (m, 2H), 2.8 (m, 1H), 3.1 (m, 2H), 3.6 (s, 2H), 7.0 (dt, 1H), 7.15 (dd, 1H), 7.30 (dd, 1H), 7.5 (d, 2H), 7.8 (d, 1H), 7.9 (s, 1H), 8.4 (d, 2H), 8.6 (d, 1H), 8.8 (s, 2H).

EXAMPLE 4

This example illustrates the preparation of 2-chloro-N-(2-{1-[4-(5-chloro-pyrimidin-2-yl)-benzyl]-piperidin-4-yl}-5-trifluoromethoxy-phenyl)-isonicotinamide (Compound A12 of Table A).

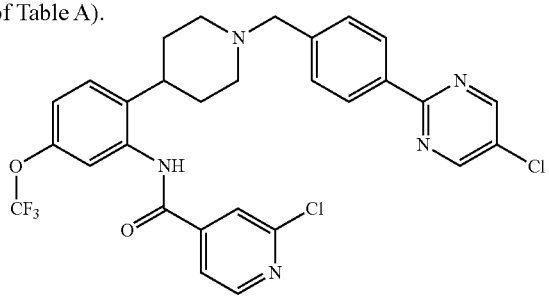

The title compound was prepared according to procedures similar to those described in Example 1 starting from 2-bromo-5-trifluoromethoxy-aniline, which was obtained as follows:

A solution of 3-trifluoromethoxy-aniline (1.77 g) in toluene (20 ml) was treated with N-bromosuccinimide (1.87 g) at ambient temperature and the reaction mixture was stirred for 2 hours at ambient temperature, quenched by addition of water and the mixture extracted with ethyl acetate (3×50 ml). The combined organic extracts were washed with aqueous sodium hydrogen carbonate (saturated), dried over sodium sulfate and then concentrated in vacuo. The residue was purified by chromatography on silica gel (eluent: cyclohexane/ethyl acetate 95:5) to afford 4-bromo-3-trifluoromethoxy-aniline (270 mg) and 2-bromo-5-trifluoromethoxy-aniline (1.45 g), which were both characterized by mass and NMR spectra. 4-bromo-3-trifluoromethoxy-aniline: MS (ES+) 256/258 (MH+); 1H NMR (400 MHz, CDCl$_3$) 3.5 (brs, 2H), 6.5 (d, 1H), 6.7 (s, 1H), 7.3 (d, 1H). 2-bromo-5-trifluoromethoxy-aniline: MS (ES+) 256/258 (MH+); 1H NMR (400 MHz, CDCl$_3$) 4.2 (brs, 2H), 6.5 (d, 1H), 6.6 (s, 1H), 7.4 (d, 1H).

The following compounds were prepared according to procedures analogous to those described in Example 1-4:

TABLE A

Compounds of formula (Ia)

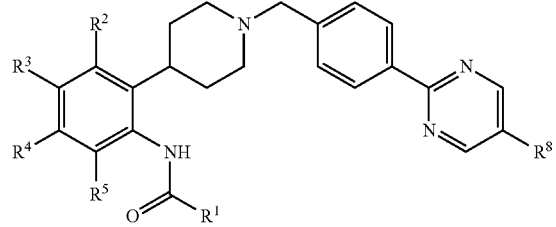

| Comp No | R$^1$ | R$^2$ | R$^3$ | R$^4$ | R$^5$ | R$^8$ | M.p. | HPLC (RT) | MS (ES+) |
|---|---|---|---|---|---|---|---|---|---|
| A1 | 2-chloro-pyrid-4-yl- | H | —CF$_3$ | H | H | Cl | 202-203° C. | 1.37 min | 586/588 |
| A2 | 2-chloro-pyrid-4-yl- | H | —CF$_3$ | H | H | F | 89-90° C. | 1.29 min | 570/572 |
| A3 | 2-chloro-5-fluoro-pyrid-4-yl- | H | —CF$_3$ | H | H | Cl | 156-158° C. | 1.38 min | 604/606 |
| A4 | 2,6-dichloro-pyrid-4-yl- | H | —CF$_3$ | H | H | Cl | 169-170° C. | 1.47 min | 620/622 |
| A5 | 2,5-dichloro-pyrid-4-yl- | H | —CF$_3$ | H | H | Cl | 147-148° C. | 1.43 min | 620/622 |
| A6 | 2-fluoro-pyrid-4-yl- | H | —CF$_3$ | H | H | Cl | 199-200° C. | 1.35 min | 570/572 |
| A7 | 2-chloro-pyrid-4-yl- | H | —CF$_3$ | H | H | H | — | 1.27 min | 552/554 |
| A8 | 2-chloro-pyrid-4-yl- | H | —CF$_3$ | F | H | Cl | 200-205° C. | 1.43 min | 604/606 |
| A9 | 2-chloro-pyrid-4-yl- | F | F | H | H | Cl | 100-105° C. | 1.30 min | 554/556 |
| A10 | 2-chloro-pyrid-4-yl- | H | F | H | H | Cl | 176° C. | 1.27 min | 536/538 |

TABLE A-continued

Compounds of formula (Ia)

(Ia)

| Comp No | R¹ | R² | R³ | R⁴ | R⁵ | R⁸ | M.p. | HPLC (RT) | MS (ES+) |
|---|---|---|---|---|---|---|---|---|---|
| A11 | 2-chloro-pyrid-4-yl- | F | —CF₃ | H | H | Cl | 105-110° C. | 1.41 min | 604/606 |
| A12 | 2-chloro-pyrid-4-yl- | H | H | —OCF₃ | H | Cl | 211-212° C. | 1.39 min | 602/604 |
| A13 | 2-methoxy-pyrid-4-yl- | H | CF3 | H | H | Cl | 199-200° C. | 1.42 min | 582/584 |
| A14 | 2-methoxy-pyrid-4-yl- | H | CF3 | F | H | Cl | 205-208° C. | 1.41 min | 600/602 |
| A15 | 2-fluoro-pyrid-4-yl- | H | CF3 | F | H | Cl | 173-176° C. | 1.24 min | 588/590 |
| A16 | 2-chloro-pyrid-4-yl- | H | CF3 | H | H | CF3 | 206-206° C. | 1.42 min | 620/622 |
| A17 | 2-chloro-pyrid-4-yl- | H | CF3 | H | H | cyclo-propyl | — | 1.32 min | 592/594 |
| A18 | 2-chloro-pyrid-4-yl- | H | CF3 | H | H | Br | 199-199° C. | 1.36 min | 630/632 |
| A19 | 2-chloro-pyrid-4-yl- | CF3 | H | H | H | Cl | 168-168° C. | 1.33 min | 586/588 |
| A20 | 2-chloro-pyrid-4-yl- | H | CF3 | H | H | CN | 200-200° C. | 1.29 min | 577/579 |
| A21 | 2-chloro-pyrid-4-yl- | H | CF3 | H | H | ethynyl | 188-188° C. | 1.31 min | 576/578 |
| A22 | 2-chloro-pyrid-4-yl- | H | CF3 | H | H | CH3 | — | 1.26 min | 566/568 |
| A23 | 2,6-dichloro-pyrid-4-yl- | H | CF3 | F | H | Cl | 198-202° C. | 1.48 min | 638/640 |
| A24 | 2,5-dichloro-pyrid-4-yl- | H | CF3 | F | H | Cl | 178-181° C. | 1.44 min | 638/640 |
| A25 | 2-chloro-5-fluoro-pyrid-4-yl- | H | CF3 | F | H | Cl | 192-194° C. | 1.44 min | 622/624 |
| A26 | 2-chloro-pyrid-4-yl- | H | H | CF3 | H | Cl | — | 1.36 min | 586/588 |
| A27 | 2-chloro-pyrid-4-yl- | H | O—CF3 | H | H | Cl | — | 1.39 min | 602/604 |
| A28 | 2-chloro-pyrid-4-yl- | H | F | F | F | Cl | 205-207° C. | 1.34 min | 572/574 |
| A29 | 2,5-dichloro-pyrid-4-yl- | H | CF3 | H | H | Cl | 182-183° C. | 1.33 min | 588/590 |
| A30 | 2,6-dichloro-pyrid-4-yl- | F | Cl | H | H | Cl | 121-125° C. | 1.42 min | 604/606 |
| A31 | 2-fluoro-pyrid-4-yl- | F | Cl | H | H | Cl | 136-138° C. | 1.28 min | 554/556 |
| A32 | 2-chloro-5-fluoro-pyrid-4-yl- | F | Cl | H | H | Cl | 124-126° C. | 1.33 min | 588/590 |
| A33 | 2-methoxy-pyrid-4-yl- | F | Cl | H | H | Cl | 208-212° C. | 1.30 min | 566/568 |
| A34 | 2,5-dichloro-pyrid-4-yl- | F | Cl | H | H | Cl | 188-191° C. | — | — |
| A35 | 2-chloro-pyrid-4-yl- | F | Cl | H | H | Cl | 119-123° C. | — | — |
| A36 | 2-chloro-pyrid-4-yl- | H | F | F | H | Cl | — | 1.27 min | 554/556 |
| A37 | 2-chloro-pyrid-4-yl- | O—CF3 | H | H | H | Cl | 74-74° C. | 1.38 min | 602/604 |

TABLE A-continued

Compounds of formula (Ia)

(Ia)

| Comp No | R¹ | R² | R³ | R⁴ | R⁵ | R⁸ | M.p. | HPLC (RT) | MS (ES+) |
|---|---|---|---|---|---|---|---|---|---|
| A38 | 2-chloro-5-fluoro-pyrid-4-yl- | H | CF3 | F | H | F | 195-198° C. | 1.38 min | 606/608 |
| A39 | 2-chloro-5-fluoro-pyrid-4-yl- | H | F | Cl | H | Cl | 208-212° C. | 1.38 min | 588/590 |
| A40 | 2-chloro-5-fluoro-pyrid-4-yl- | H | F | Cl | H | F | 191-194° C. | 1.31 min | 572/574 |
| A41 | 2-chloro-5-fluoro-pyrid-4-yl- | H | CF3 | H | H | F | 128-130° C. | 1.30 min | 588/590 |
| A42 | 2-chloro-5-fluoro-pyrid-4-yl- | F | CF3 | H | H | F | 71-74° C. | 1.39 min | 606/608 |
| A43 | 2-chloro-5-fluoro-pyrid-4-yl- | F | CF3 | H | H | Cl | 128-132° C. | 1.42 min | 622/624 |
| A44 | 2,5-dichloro-pyrid-4-yl- | H | F | Cl | H | F | 197-199° C. | 1.34 min | 588/590 |
| A45 | 2,5-dichloro-pyrid-4-yl- | H | CF3 | F | H | F | 198-200° C. | 1.42 min | 622/624 |
| A46 | 2,5-dichloro-pyrid-4-yl- | F | CF3 | H | H | F | 74-76° C. | 1.39 min | 622/624 |
| A47 | 2,5-dichloro-pyrid-4-yl- | H | F | Cl | H | Cl | 179-200° C. | 1.41 min | 604/606 |
| A48 | 2,5-dichloro-pyrid-4-yl- | F | CF3 | H | H | Cl | 98-103° C. | 1.43 min | 638/640 |
| A49 | 2,5-dichloro-pyrid-4-yl- | H | CF3 | H | H | F | 179-183° C. | 1.33 min | 604/606 |
| A50 | 2,5-difluoro-pyrid-4-yl- | H | F | Cl | H | F | 177-178° C. | 1.29 min | 556/558 |
| A51 | 2,5-difluoro-pyrid-4-yl- | H | F | Cl | H | Cl | 188-189° C. | 1.33 min | 572/574 |
| A52 | 2,5-difluoro-pyrid-4-yl- | H | CF3 | F | H | F | 178-179° C. | 1.35 min | 590 |
| A53 | 2,5-difluoro-pyrid-4-yl- | H | CF3 | F | H | Cl | 181-182° C. | 1.41 min | 606/608 |
| A54 | 2,5-difluoro-pyrid-4-yl- | F | CF3 | H | H | F | 144-145° C. | 1.32 min | 590 |
| A55 | 2,5-difluoro-pyrid-4-yl- | F | CF3 | H | H | Cl | 151-152° C. | 1.38 min | 606/608 |
| A56 | 2,5-difluoro-pyrid-4-yl- | H | CF3 | H | H | F | 193-194° C. | 1.29 min | 572 |
| A57 | 2-chloro-pyrid-4-yl- | H | F | Cl | H | F | 176-177° C. | 1.28 min | 554/556 |
| A58 | 2-chloro-pyrid-4-yl- | H | F | Cl | H | Cl | 189-190° C. | 1.33 min | 570/572 |

TABLE A-continued

Compounds of formula (Ia)

[Structure of formula (Ia)]

| Comp No | R¹ | R² | R³ | R⁴ | R⁵ | R⁸ | M.p. | HPLC (RT) | MS (ES+) |
|---|---|---|---|---|---|---|---|---|---|
| A59 | 2-chloro-pyrid-4-yl- | H | CF3 | F | H | F | 163-166° C. | 1.35 min | 588/590 |
| A60 | 2-chloro-pyrid-4-yl- | F | CF3 | H | H | F | 94-96° C. | 1.33 min | 588/590 |

EXAMPLE 5

This example illustrates the preparation of 2-chloro-N-{1'-[4-(5-chloro-pyrimidin-2-yl)-benzyl]-6-trifluoromethyl-1',2',3',4',5',6'-hexahydro-[2,4']bipyridinyl-3-yl}-isonicotinamide (Compound B1 of Table B)

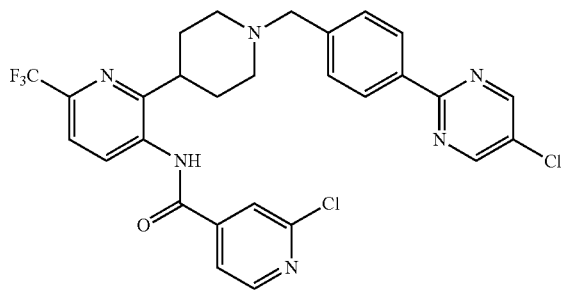 [SMILES: O=C(Nc1ccc(C(F)(F)F)nc1C1CCN(Cc2ccc(-c3ncc(Cl)cn3)cc2)CC1)c1ccnc(Cl)c1]

Step A:

A solution of 3-amino-2-chloro-6-trifluoromethyl-pyridine (0.890 g), 4-(4,4,5,5-tetramethyl-[1,3,2]dioxaborolan-2-yl)-3,6-dihydro-2H-pyridine-1-carboxylic acid tert-butyl ester (1.4 g) (prepared as described in WO 2006/003494) and tetrakis(triphenyl-phosphine)palladium (0.200 g) in 1,2-dimethoxyethane (45 ml) was treated with aqueous potassium phosphate (1.1 M) (1.92 g). The reaction mixture was stirred at 80° C. for 3 hours. Aqueous workup with ethyl acetate furnished a residue which was purified by chromatography on silica gel (eluent: hexane/ethyl acetate 1:1) to give 3-amino-6-trifluoromethyl-3',6'-dihydro-2'H-[2,4']bipyridinyl-1'-carboxylic acid tert-butyl ester (1.5 g) as a white solid. MS (ES+) 288 (M-isoprene); 1H NMR (400 MHz, CDCl₃) 1.50 (s, 9H), 2.61 (m, 2H), 3.67 (t, 2H), 4.10 (m, 2H), 4.21 (s, 2H), 6.11 (s, 1H), 7.03 (d, 1H), 7.33 (d, 1H).

Step B:

The product obtained in Step A (1 g) was dissolved in ethanol (40 ml) and after degassing, palladium on charcoal (10% by weight) (100 mg) was added. Under a hydrogen atmosphere, the reaction mixture was stirred at ambient temperature for 2 days. Filtration on Celite® furnished 3-amino-6-trifluoromethyl-3',4',5',6'-tetrahydro-2'H-[2,4']bipyridinyl-1'-carboxylic acid tert-butyl ester (1 g) as white solid. MS (ES+) 290/292 (M-isoprene); 1H NMR (400 MHz, CDCl₃) 1.48 (s, 9H), 1.85 (m, 4H), 2.77 (m, 1H), 2.88 (m, 2H), 3.97 (s, 2H), 4.24 (m, 2H), 6.97 (d, 1H), 7.32 (d, 1H).

Step C:

A solution of the product obtained in Step C (1 g) in toluene (40 ml) was treated with N,N-diisopropylethylamine (1.05 ml) and then 2-chloro-isonicotinoyl chloride. The 2-chloro-isonicotinoyl chloride was prepared from 2-chloro-isonicotinic acid (0.496 g) and oxalyl chloride (0.346 ml) in dichloromethane (40 ml). The reaction mixture was stirred at ambient temperature for 2 hours, poured into aqueous sodium hydrogen carbonate (saturated), extracted with ethyl acetate, washed with water, dried over sodium sulfate and then concentrated in vacuo. The residue was purified by chromatography on silica gel (eluent: hexane/ethyl acetate 1:1) to afford 3-[(2-chloro-pyridine-4-carbonyl)-amino]-6-trifluoromethyl-3',4',5',6'-tetrahydro-2'H-[2,4']bipyridinyl-1'-carboxylic acid tert-butyl ester (1.1 g). MS (ES+) 485/487 (MH+), 429/431 (M-isoprene); 1H NMR (400 MHz, CDCl₃) 1.47 (s, 9H), 1.79 (m, 2H), 1.96 (m, 2H), 2.88 (m, 2H), 2.95 (m, 1H), 4.25 (m, 2H), 7.61 (d, 1H), 7.66 (m, 1H), 7.79 (s, 1H), 8.05 (s, 1H), 8.32 (d, 1H), 8.64 (d, 1H).

Step D:

A solution of the compound obtained in Step C (300 mg) in dichloromethane (15 ml) was treated with trifluoroacetic acid (1.2 ml) at ambient temperature for 1 hour. Evaporation of the solvent and drying of the solid at high vacuum afforded 2-chloro-N-(6-trifluoromethyl-1',2',3',4',5',6'-hexahydro-[2,4']bipyridinyl-3-yl)-isonicotinamide trifluoroacetate. The free base was obtained by partitioning between ethyl acetate and aqueous sodium hydrogen carbonate (saturated).

Step E:

The product obtained in Step D (free base, 288 mg) was mixed with 445-chloro-pyrimidin-2-yl)-benzaldehyde (Preparation 1, 165 mg) and dissolved in tetrahydrofuran (20 ml). The solution was stirred under an argon atmosphere and treated with sodium cyanoborohydride (475 mg). The reaction mixture was stirred for 16 hours at ambient temperature and quenched by addition of water. The acetate salt (Compound F1 of Table F) was isolated by extraction with ethyl acetate, drying over sodium sulfate and evaporation of the solvents. The free base was obtained by partitioning between ethyl acetate and aqueous sodium hydrogen carbonate (saturated). The organic layer was dried over sodium sulfate and concentrated in vacuo to give a residue, which was purified by chromatography on silica gel (eluent: ethyl acetate/cyclohexane 4:6) to afford the title compound as a yellow solid (120 mg). M.p. 98° C. MS (ES+) 587/589 (MH+); 1H NMR (400 MHz, CDCl₃) 1.7 (m, 2H), 2.1 (m, 4H), 2.7 (m, 1H), 3.0 (m, 2H), 3.6 (s, 2H), 7.4 (d, 2H), 7.5 (d, 2H), 7.55 (m, 1H), 7.60 (d, 1H), 7.70 (s, 1H), 7.8 (br s, 1H), 8.3 (d, 2H), 8.4 (m, 1H), 8.6 (d, 12H), 8.7 (s, 2H).

EXAMPLE 6

This example illustrates the preparation of 2-chloro-N-{1'-[4-(5-fluoro-pyrimidin-2-yl)-benzyl]-6-trifluoromethyl-1', 2',3',4',5',6'-hexahydro-[2,4']bipyridinyl-3-yl}-isonicotinamide (Compound B2 of Table B)

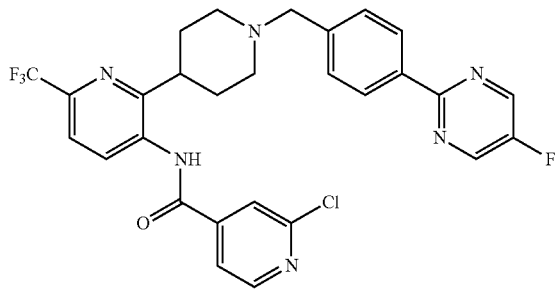 [SMILES: O=C(Nc1ccc(C(F)(F)F)nc1C1CCN(Cc2ccc(-c3ncc(F)cn3)cc2)CC1)c1ccnc(Cl)c1]

The title compound was prepared according to a procedure similar to those described in Example 5 using 4-(5-fluoro-pyrimidin-2-yl)-benzaldehyde (Preparation 2) in Step E. M.p. 82-83° C. The acetate salt (Compound F2 of Table F) was also isolated.

EXAMPLE 7

This example illustrates the preparation of 2-chloro-N-{1'-[4-(5-chloro-pyrimidin-2-yl)-benzyl]-6-difluoromethoxy-1', 2',3',4',5',6'-hexahydro-[2,4']bipyridinyl-3-yl}-isonicotinamide (Compound B6 of Table B).

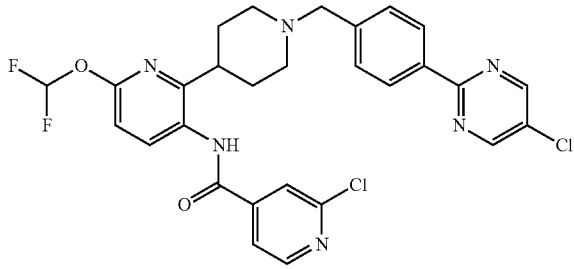 [SMILES: O=C(Nc1ccc(OC(F)F)nc1C1CCN(Cc2ccc(-c3ncc(Cl)cn3)cc2)CC1)c1ccnc(Cl)c1]

The title compound was obtained from 2-bromo-6-difluoromethoxy-pyridin-3-yl-amine following the procedures described in Example 5. 2-Bromo-6-difluoromethoxy-pyridin-3-yl-amine was prepared as follows:
Step A:
2-Hydroxy-5-nitro-pyridine (5 g) was treated with sodium chlorodifluoro-acetate (11.5 g) in refluxing acetonitrile (186 ml) for 2 days. The solvent was evaporated, the residue poured into ethyl acetate, washed with brine, dried over sodium sulfate and then concentrated in vacuo. Chromatography on silica gel (eluent: hexane/ethyl acetate 1:1) afforded 2-difluoromethoxy-5-nitro-pyridine (1 g) and 1-difluoromethyl-5-nitro-1H-pyridin-2-one (90 mg). 2-Difluoromethoxy-5-nitro-pyridine: MS (ES+) 191 (MH+); 1H NMR (400 MHz, CDCl₃) 7.05 (d, 1H), 7.51 (t, 1H), 8.53 (dd, 1H), 9.09 (d, 1H). 1-Difluoromethyl-5-nitro-1H-pyridin-2-one: MS (ES+) 191 (MH+); ¹H NMR (400 MHz, CDCl₃) 6.65 (d, 1H), 7.63 (t, 1H), 8.14 (dd, 1H), 8.73 (d, 1H).
Step B:
2-Difluoromethoxy-5-nitro-pyridine obtained in Step A (1.6 g) was treated with iron (5 g) and concentrated hydrochloric acid (0.23 ml) in ethanol (15 ml) and water (2.5 ml) at 80° C. for 20 minutes. Filtration over Celite® and evaporation of the solvent afforded 6-difluoromethoxy-pyridin-3-yl-amine (1.4 g) as an orange solid. 1H NMR (400 MHz, CDCl₃) 3.51 (br s, 2H), 6.89 (d, 1H), 7.23 (d, 1H), 7.44 (dd, 1H), 7.80 (d, 1H).
Step C:
6-Difluoromethoxy-pyridin-3-yl-amine obtained in Step B (1.36 g) was treated with N-bromosuccinimide (1.51 g) in acetonitrile for 10 minutes. The solution was poured into water, extracted with ethyl acetate, the organic layer dried over sodium sulfate and concentrated in vacuo. Chromatography on silica gel (eluent: cyclohexane/ethyl acetate 7:3) afforded 2-bromo-6-difluoromethoxy-pyridin-3-yl-amine as a red oil. 1H NMR (400 MHz, CDCl₃) 3.95 (br s, 2H), 6.72 (d, 1H), 7.07 (d, 1H), 7.24 (dd, 1H).

EXAMPLE 8

This example illustrates the preparation of 2-chloro-N-{1'-[4-(5-chloro-pyrimidin-2-yl)-benzyl]-4-fluoro-6-trifluoromethyl-1',2',3',4',5',6'-hexahydro-[2,4']bipyridinyl-3-yl}-isonicotinamide (Compound B7 of Table B).

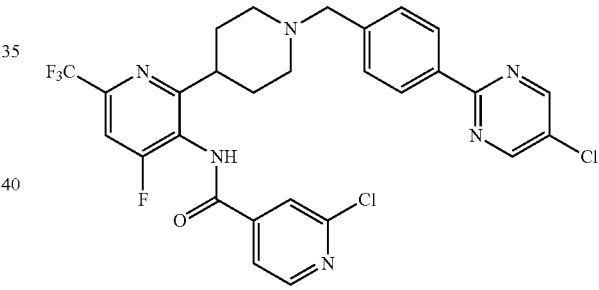

Step A:
A solution of the compound obtained in Step B of Example 5 (10.35 g) and N-chlorosuccinimide (4.4 g) in N-methylpyrrolidinone (150 ml) was stirred at ambient temperature for 2.5 hours. The reaction mixture was poured into water, and extracted several times with ethyl acetate. The combined organic layers were washed with brine, dried over sodium sulfate and then concentrated in vacuo. Chromatography on silica gel (eluent: hexane/ethyl acetate 1:1) afforded 3-amino-4-chloro-6-trifluoromethyl-3',4',5',6'-tetrahydro-2'H-[2,4'] bipyridinyl-1'-carboxylic acid tert-butyl ester (9.6 g) as a foam. MS (ES+) 380/382 (MH+), 324/326 (M-isoprene); 1H NMR (400 MHz, CDCl₃) 1.48 (s, 9H), 1.85 (m, 4H), 2.82 (m, 3H), 4.24 (m, 2H), 4.41 (br s, 2H), 7.46 (s, 1H).
Step B:
A solution of the compound obtained in Step A (7.6 g) and trifluoroacetic acid (61.7 ml) in dichloromethane (380 ml) was heated to 55° C. At this temperature, aqueous hydrogen peroxide (30% by weight) (23 ml) was slowly added over a period of 30 minutes. The reaction mixture was kept at this temperature for a further 2 hours. The reaction mixture was poured into water and extracted several times with dichloromethane. The combined organic extracts were washed with brine, dried over sodium sulfate, and then concentrated in vacuo. The residue was re-dissolved in dichloromethane (200 ml). Di-tert-butyl-dicarbonate (5.4 g) and N,N-diisopropyl-ethylamine (14.2 ml) were subsequently added and the reaction mixture was stirred at ambient temperature for 16 hours. The reaction mixture was quenched by addition of water and extracted with dichloromethane. The combined organic extracts were washed with brine, dried over sodium sulfate and concentrated in vacuo. Chromatography on silica gel (eluent: hexane/ethyl acetate 5:1) afforded 4-chloro-3-nitro-6-trifluoromethyl-3',4',5',6'-tetrahydro-2'H-[2,4']bipyridinyl-1'-carboxylic acid tert-butyl ester (4.9 g) as a foam. MS (ES+) 410/412 (MH+), 354/356 (M-isoprene); 1H NMR (400 MHz, CDCl$_3$) 1.48 (s, 9H), 1.77 (m, 2H), 1.95 (m, 2H), 2.85 (m, 3H), 4.26 (m, 2H), 7.74 (s, 1H).

Step C:

A solution of the compound obtained in Step B (1.2 g) and spray dried potassium fluoride (339 mg) in dimethyl sulfoxide (57 ml) was stirred at 80° C. for 1 hour. The reaction mixture was poured into water and extracted several times with ethyl acetate. The combined organic extracts were washed with brine, dried over sodium sulfate and concentrated in vacuo. Chromatography on silica gel (eluent: hexane/ethyl acetate 5:1) afforded 4-fluoro-3-nitro-6-trifluoromethyl-3',4',5',6'-tetrahydro-2'H-[2,4']bipyridinyl-1'-carboxylic acid tert-butyl ester (0.7 g) as a foam. MS (ES+) 338/339 (M-isoprene); 1H NMR (400 MHz, CDCl$_3$) 1.48 (s, 9H), 1.79 (m, 2H), 1.94 (m, 2H), 2.79 (m, 2H), 2.99 (m, 1H), 4.26 (m, 2H), 7.51 (d, 1H).

Step D:

The compound obtained in Step C (1.8 g) was dissolved in ethanol (48 ml) and after degassing, palladium on charcoal (10% by weight) (500 mg) was added. Under a hydrogen atmosphere, the reaction mixture was stirred at ambient temperature for 1 day. Filtration on Celite® furnished 3-amino-4-fluoro-6-trifluoromethyl-3',4',5',6'-tetrahydro-2'H-[2,4']bipyridinyl-1'-carboxylic acid tert-butyl ester (1.6 g) as a white solid. MS (ES+) 364/365 (MH+), 308/309 (M-isoprene); 1H NMR (400 MHz, CDCl$_3$) 1.48 (s, 9H), 1.85 (m, 4H), 2.86 (m, 3H), 3.90 (br s, 2H), 4.25 (m, 2H), 7.22 (d, 1H).

The compound obtained in Step D was then treated according to the procedures described in Example 5 (Steps C-E) to obtain the title compound.

EXAMPLE 9

This example illustrates the preparation of 2-chloro-N-{5,6-dichloro-1'-[4-(5-chloro-pyrimidin-2-yl)-benzyl]-1',2',3',4',5',6'-hexahydro-[2,4']bipyridinyl-3-yl}-isonicotinamide (Compound B8 of Table B).

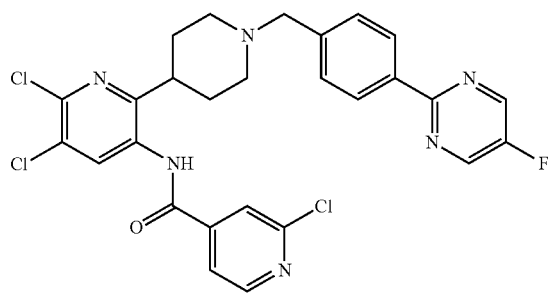 [SMILES: O=C(Nc1cc(Cl)c(Cl)nc1C1CCN(Cc2ccc(-c3ncc(F)cn3)cc2)CC1)c1ccnc(Cl)c1]

The title compound was prepared from 3-amino-5,6-dichloro-3',4',5',6'-tetrahydro-2'H-[2,4']bipyridinyl-1'-carboxylic acid tert-butyl ester according to procedures analogous to those described in Example 5, Steps C-E. 3-Amino-5,6-dichloro-3',4',5',6'-tetrahydro-2'H-[2,4']bipyridinyl-1'-carboxylic acid tert-butyl ester was prepared as follows:

Step A:

A degassed solution of 2,5-dichloro-3-amino-pyridine (40.75 g), 4-(4,4,5,5-tetramethyl-[1,3,2]dioxaborolan-2-yl)-3,6-dihydro-2H-pyridine-1-carboxylic acid tert-butyl ester (77.25 g) (prepared as described in WO 2006/003494) and bis(triphenylphosphine)-palladium(II) chloride (8.76 g) in dioxane (1500 ml) was treated with a degassed solution of sodium carbonate (79 g) in water (800 ml). The reaction mixture was heated to reflux for 16 hours, cooled to ambient temperature and the solvent evaporated in vacuo. The residue was partitioned between ethyl acetate and water and the aqueous layer extracted three times with ethyl acetate. The combined organic extracts were dried over sodium sulfate and concentrated in vacuo. Chromatography on silica gel (eluent: cyclohexane/ethyl acetate 8:2) afforded 3-amino-5-fluoro-3',6'-dihydro-2'H-[2,4']bipyridinyl-1'-carboxylic acid tert-butyl ester (60 g) as a yellow solid. MS (ES+) 310/311 (MH+), 254/256 (MH+-isobutene).

Step B:

The tetrahydropyridine intermediate obtained in Step A (54 g) was hydrogenated in methanol (4000 ml) at 80° C. and 100 bar hydrogen in the presence of 1,1'-bis(di-iso-propyl-phosphino)ferrocene(1,5-cyclooctadiene)rhodium(I) tetrafluoroborate (358 mg) for 20 hours to afford 3-amino-5-chloro-3',4',5',6'-tetrahydro-2'H-[2,4']bipyridinyl-1'-carboxylic acid tert-butyl ester (44 g). MS (ES+) 312/314 (MH+).

Step C:

The product obtained in Step B (43 g) was dissolved in N-methylpyrrolidone (600 ml) and treated with N-chlorosuccinimide (19 g) at ambient temperature for 20 hours. The reaction mixture was then diluted with diethyl ether and washed several times with water. The aqueous layer was extracted with ethyl acetate and the combined organic extracts dried over sodium sulfate. The solvent was removed in vacuo and the residue purified by chromatography on silica gel (eluent: dichloromethane) to afford 3-amino-5,6-dichloro-3',4',5',6'-tetrahydro-2'H-[2,4']bipyridinyl-1'-carboxylic acid tert-butyl ester (43 g) as a solid. MS (ES+) 312/314 (MH+).

Alternatively, 3-amino-5,6-dichloro-3',4',5',6'-tetrahydro-2'H-[2,4']bipyridinyl-1'-carboxylic acid tert-butyl ester could be obtained as described in WO 2006/003494 using a Negishi coupling between 2,5-dichloro-3-amino-pyridine and 4-iodo-piperidine 1-carboxylic acid tert-butyl ester.

The following compounds were prepared according to procedures analogous to those described in Example 5-9:

TABLE B

Compounds of formula (Ib)

(Ib)

[Structure: R³, R⁴, R⁵ substituted pyridine connected to piperidine-CH2-phenyl-pyrimidine with R⁸, with NHC(O)R¹ group]

| Comp No | R¹ | R³ | R⁴ | R⁵ | R⁸ | M.p. | HPLC (RT) | MS (ES+) |
|---|---|---|---|---|---|---|---|---|
| B1 | 2-chloro-pyrid-4-yl- | —CF₃ | H | H | Cl | 97-98° C. | 1.34 min | 587/589 |
| B2 | 2-chloro-pyrid-4-yl- | —CF₃ | H | H | F | 89-90° C. | 1.28 min | 571/573 |
| B3 | 5-chloro-2-fluoro-pyrid-4-yl- | —CF₃ | H | H | Cl | — | 1.37 min | 605/607 |
| B4 | 2-chloro-5-fluoro-pyrid-4-yl- | —CF₃ | H | H | Cl | 214-216° C. | 1.38 min | 605/607 |
| B5 | 2-chloro-pyrid-4-yl- | —CF₃ | H | H | H | — | 1.27 min | 553/555 |
| B6 | 2-chloro-pyrid-4-yl- | —OCHF₂ | H | H | Cl | 182-188° C. | 1.34 min | 585/587 |
| B7 | 2-chloro-pyrid-4-yl- | —CF₃ | H | F | Cl | — | 1.39 min | 605/607 |
| B8 | 2-chloro-pyrid-4-yl- | Cl | Cl | H | Cl | 197° C. | 1.35 min | 589/591 |
| B9 | 2-chloro-pyrid-4-yl- | CF3 | H | H | cyclopropyl | — | 1.33 min | 593/595 |
| B10 | 2-chloro-pyrid-4-yl- | CF3 | H | H | Br | 180-180° C. | 1.36 min | 631/633 |
| B11 | 2-chloro-pyrid-4-yl- | CF3 | H | H | CH3 | — | 1.25 min | 567/569 |
| B12 | 2,5-difluoro-pyrid-4-yl- | CF3 | H | H | Cl | 188-189° C. | 1.34 min | 589/591 |
| B13 | 2-chloro-5-fluoro-pyrid-4-yl- | CF3 | H | H | F | 197-201° C. | 1.38 min | 589/591 |
| B14 | 2-chloro-5-fluoro-pyrid-4-yl- | O—CHF2 | H | H | Cl | 169-172° C. | 1.36 min | 603/605 |
| B15 | 2-chloro-5-fluoro-pyrid-4-yl- | O—CHF2 | H | H | F | 165-168° C. | 1.30 min | 587/589 |
| B16 | 2,5-difluoro-pyrid-4-yl- | CF3 | H | H | F | 197-198° C. | 1.31 min | 573 |
| B17 | 2,5-dichloro-pyrid-4-yl- | CF3 | H | H | F | 160-163° C. | 1.35 min | 605/607 |
| B18 | 2,5-dichloro-pyrid-4-yl- | CF3 | H | H | Cl | 93-96° C. | 1.41 min | 621/623 |
| B19 | 2,5-difluoro-pyrid-4-yl- | Cl | Cl | H | F | 222-223° C. | 1.34 min | 573/575 |
| B20 | 2,5-difluoro-pyrid-4-yl- | O—CHF2 | H | H | F | 173-174° C. | 1.25 min | 571 |
| B21 | 2,5-difluoro-pyrid-4-yl- | O—CHF2 | H | H | Cl | 170-171° C. | 1.31 min | 587/589 |
| B22 | 2,5-difluoro-pyrid-4-yl- | Cl | Cl | H | Cl | 232-237° C. | 1.38 min | 589/591 |
| B23 | 2-chloro-5-fluoro-pyrid-4-yl- | Cl | Cl | H | F | 225-229° C. | 1.36 min | 589/591 |
| B24 | 2,5-dichloro-pyrid-4-yl- | O—CHF2 | H | H | Cl | 79-83° C. | 1.36 min | 619/621 |
| B25 | 2,5-dichloro-pyrid-4-yl- | O—CHF2 | H | H | F | 204-206° C. | 1.31 min | 603/605 |
| B26 | 2-chloro-pyrid-4-yl- | Cl | Cl | H | F | 128-131° C. | 1.30 min | 571/573 |

EXAMPLE 10

This example illustrates the preparation of 2-chloro-N-(2-{1-[4-(5-chloro-pyrimidin-2-yl)-benzyl]-1-oxy-piperidin-4-yl}-4-trifluoromethyl-phenyl)-isonicotinamide (Compound C1 of Table C)

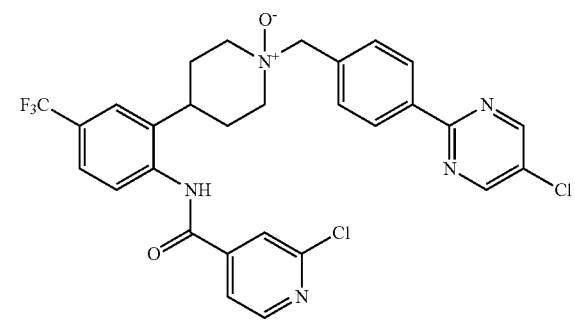 [SMILES: O=C(Nc1ccc(C(F)(F)F)cc1C1CC[N+]([O-])(Cc2ccc(-c3ncc(Cl)cn3)cc2)CC1)c1ccnc(Cl)c1]

A solution of 2-chloro-N-(2-{1-[4-(5-chloro-pyrimidin-2-yl)-benzyl]-1-oxy-piperidin-4-yl}-4-trifluoromethyl-phenyl)-isonicotinamide (270 mg, Example 1) in dichloromethane (12 ml) was treated with 3-chloro-peroxybenzoic acid (92 mg) at ambient temperature. The solution was stirred at ambient temperature for 16 hours and the precipitate collected by filtration. The solid obtained was rinsed with diethyl ether and dried under high vacuum to afford the title compound as a white powder. M.p. 193-194° C. MS (ES+) 603/605 (MH+).

The following compounds were prepared according to procedures analogous to the one described in Example 10:

TABLE C

Compounds of formula (Ic)

(Ic)

[Structure with R², R³, R⁴, R⁵ on phenyl ring, piperidine N-oxide, linker to pyrimidine with R⁸]

| Comp No | R¹ | R² | R³ | R⁴ | R⁵ | R⁸ | M.p. |
|---|---|---|---|---|---|---|---|
| C1 | 2-chloro-pyrid-4-yl- | H | —CF₃ | H | H | Cl | 193-194° C. |
| C2 | 2-chloro-pyrid-4-yl- | H | —CF₃ | H | H | F | 178-179° C. |
| C3 | 2-chloro-5-fluoro-pyrid-4-yl- | H | —CF₃ | H | H | Cl | 198-199° C. |
| C4 | 2-chloro-pyrid-4-yl- | H | —CF₃ | F | H | Cl | 196-197° C. |
| C5 | 2-chloro-pyrid-4-yl- | F | —F | H | H | Cl | 183-184° C. |
| C6 | 2-chloro-pyrid-4-yl- | F | —CF₃ | H | H | Cl | 207-209° C. |
| C7 | 2-fluoro-pyrid-4-yl- | H | CF3 | F | H | Cl | 193-196° C. |
| C8 | 2-methoxy-pyrid-4-yl- | H | CF3 | F | H | Cl | 183-186° C. |
| C9 | 2,6-dichloro-pyrid-4-yl- | H | CF3 | F | H | Cl | 193-196° C. |
| C10 | 2,5-dichloro-pyrid-4-yl- | H | CF3 | F | H | Cl | 188-192° C. |
| C11 | 2-chloro-5-fluoro-pyrid-4-yl- | H | CF3 | F | H | Cl | 184-187° C. |
| C12 | 2,6-dichloro-pyrid-4-yl- | F | Cl | H | H | Cl | 194-197° C. |
| C13 | 2-fluoro-pyrid-4-yl- | F | Cl | H | H | Cl | >220° C. |
| C14 | 2-chloro-5-fluoro-pyrid-4-yl- | F | Cl | H | H | Cl | 191-195° C. |
| C15 | 2-methoxy-pyrid-4-yl- | F | Cl | H | H | Cl | 183-187° C. |
| C16 | 2-chloro-pyrid-4-yl- | F | Cl | H | H | Cl | 199-205° C. |
| C17 | 2,5-dichloro-pyrid-4-yl- | F | Cl | H | H | Cl | 208-211° C. |

EXAMPLE 11

This example illustrates the preparation of 2-chloro-N-{1'-[4-(5-chloro-pyrimidin-2-yl)-benzyl]-6-methyl-1',2',3',4',5',6'-hexahydro-[2,4']bipyridinyl-3-yl}-isonicotinamide (Compound D1 of Table D)

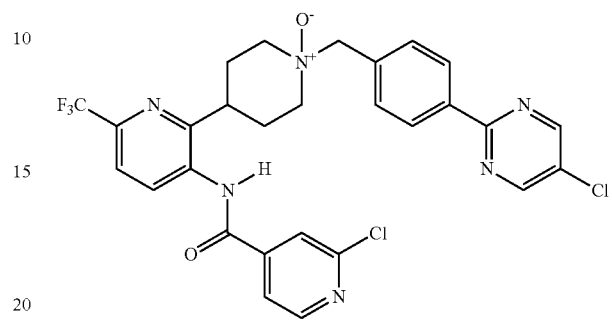

A solution of 2-chloro-N-{1'-[4-(5-chloro-pyrimidin-2-yl)-benzyl]-6-methyl-1',2',3',4',5',6'-hexahydro-[2,4]bipyridinyl-3-yl}-isonicotinamide (188 mg, Example 5) in dichloromethane (8 ml) was treated with 3-chloro-peroxybenzoic acid (65 mg) at ambient temperature. The solution was stirred at ambient temperature overnight and the precipitate collected by filtration. The solid obtained was rinsed with diethyl ether and dried under high vacuum to afford the title compound (170 mg) as a white powder. M.p. 177° C. MS (ES+) 603/605 (MH+).

The following compounds were prepared according to procedures analogous to the one described in Example 11:

TABLE D

Compounds of formula (Id)

(Id)

[Structure with R³, R⁴, R⁵ on pyridine ring, piperidine N-oxide, linker to pyrimidine with R⁸]

| Comp No | R¹ | R³ | R⁴ | R⁵ | R⁸ | M.p. |
|---|---|---|---|---|---|---|
| D1 | 2-chloro-pyrid-4-yl- | —CF₃ | H | H | Cl | 177° C. |
| D2 | 2-chloro-pyrid-4-yl- | —CF₃ | H | H | F | 201° C. |
| D3 | 5-chloro-2-fluoro-pyrid-4-yl- | —CF₃ | H | H | Cl | 183-185° C. |
| D4 | 2-chloro-5-fluoro-pyrid-4-yl- | —CF₃ | H | H | Cl | 173-175° C. |
| D5 | 2-chloro-pyrid-4-yl | —CF₃ | H | F | Cl | 222-224° C. |

The preparation of the following salts E1 and E2 in Table E has been described in Example 1 and Example 2, respectively. Other salts can be prepared according to procedures analogous to the one described in Example 12 below:

EXAMPLE 12

This example illustrates the preparation of 2-chloro-N-(2-{1-[4-(5-chloro-pyrimidin-2-yl)-benzyl]-piperidin-4-yl}-4-trifluoromethyl-phenyl)-isonicotinamide hydrochloride (Compound E3 of Table E)

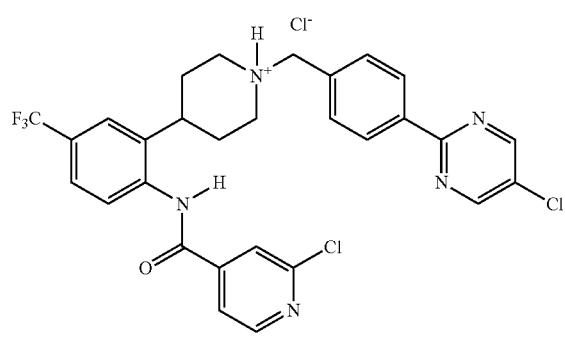 [SMILES: [Cl-] ; O=C(Nc1ccc(C(F)(F)F)cc1C1CC[NH+](Cc2ccc(-c3ncc(Cl)cn3)cc2)CC1)c1ccnc(Cl)c1]

A solution of 2-chloro-N-(2-{1-[4-(5-chloro-pyrimidin-2-yl)-benzyl]-piperidin-4-yl}-4-trifluoromethyl-phenyl)-isonicotinamide (1 g, Example 1) in dichloromethane (50 ml) was treated with hydrochloric acid gas for 2 min. The white solid formed was rinsed with diethyl ether and dried under high vacuum to afford the title compound (1 g) as a white powder. M.p. 282-283° C.

TABLE E

Compounds of formula (Ie)

(Ie)

| Comp No | $R^1$ | $R^2$ | $R^3$ | $R^4$ | $R^5$ | $R^8$ | HX | M.p. |
|---|---|---|---|---|---|---|---|---|
| E1 | 2-chloro-pyrid-4-yl- | H | —CF$_3$ | H | H | Cl | CH$_3$CO$_2$H | 222-223° C. |
| E2 | 2-chloro-pyrid-4-yl- | H | —CF$_3$ | H | H | F | CH$_3$CO$_2$H | 154° C. |
| E3 | 2-chloro-pyrid-4-yl- | H | —CF$_3$ | H | H | Cl | HCl | 282-283° C. |
| E4 | 2-chloro-pyrid-4-yl- | H | CF3 | H | H | Cl | 2-Hydroxy-benzoic acid | 225° C. |
| E5 | 2-chloro-pyrid-4-yl- | H | CF3 | H | H | Cl | 2,3,4,5-Tetrahydroxy-6-oxo-hexanoic acid | 165° C. |
| E6 | 2-chloro-pyrid-4-yl- | H | CF3 | H | H | Cl | 2-Chloro-benzoic acid | 166° C. |
| E7 | 2-chloro-pyrid-4-yl- | H | CF3 | H | H | Cl | Phosphoric acid | 125° C. |
| E8 | 2-chloro-pyrid-4-yl- | H | CF3 | H | H | Cl | 3-Hydroxy-propane-1-sulfonic acid | 183° C. |
| E9 | 2-chloro-pyrid-4-yl- | H | CF3 | H | H | Cl | Ethanesulfonic acid | 260° C. |
| E10 | 2-chloro-pyrid-4-yl- | H | CF3 | H | H | Cl | Toluene-4-sulfonic acid | 242° C. |

The preparation of the following salts has been described in Example 5 and Example 6, respectively:

TABLE F

Compounds of formula (If)

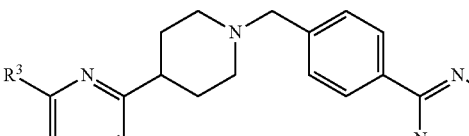

| Comp No | $R^1$ | $R^3$ | $R^4$ | $R^5$ | $R^8$ | HX | M.p. |
|---|---|---|---|---|---|---|---|
| F1 | 2-chloro-pyrid-4-yl- | —CF$_3$ | H | H | Cl | CH$_3$CO$_2$H | 254-255° C. |
| F2 | 2-chloro-pyrid-4-yl- | —CF$_3$ | H | H | F | CH$_3$CO$_2$H | 143° C. |

Preparation 1

4-(5-chloro-pyrimidin-2-yl)-benzaldehyde

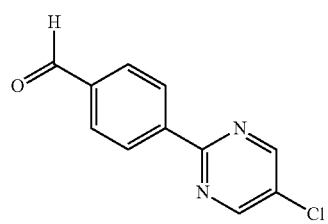 [SMILES: O=Cc1ccc(-c2ncc(Cl)cn2)cc1]

Palladium dichloro-bis(triphenylphosphine) (3.5 g) was added to a stirred solution of 4-formylbenzene boronic acid (32.5 g), 2,5-dichloro-pyrimidine (30 g) in toluene (1000 ml) and ethanol (100 ml) under an argon atmosphere. The solution was purged with argon and aqueous sodium carbonate (2N) (200 ml) was added. The reaction mixture was stirred at 60° C. for 90 minutes, cooled to ambient temperature, diluted with ethyl acetate, and washed successively with aqueous sodium hydrogen carbonate (saturated), water and brine. The combined organic extracts were treated with charcoal, dried over sodium sulfate, filtered through Hyflo® and concentrated in vacuo. The residue was triturated with diethyl ether (100 ml), the solid isolated by filtration and dried under high vacuum to give 4-(5-chloro-pyrimidin-2-yl)-benzaldehyde as a white solid. M.p. 186° C. 1H NMR (400 MHz, DMSO) 8.10 (d, 2H), 8.55 (d, 2H), 9.1 (s, 2H).

Preparation 2

4-(5-fluoro-pyrimidin-2-yl)-benzaldehyde

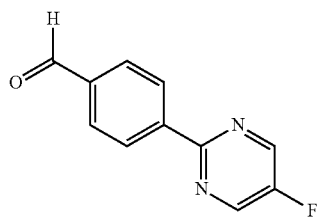 [SMILES: O=Cc1ccc(-c2ncc(F)cn2)cc1]

The title compound was prepared according to a procedure similar to the one described in Preparation 1, starting from 2-chloro-5-fluoro-pyrimidine to give 4-(5-chloro-pyrimidin-2-yl)benzaldehyde as a white solid. MS (ES+) 203 (MH$^+$); 1H NMR (400 MHz, CDCl$_3$) 8.0 (d, 2H), 8.6 (d, 2H), 28.75 (s, 2H).

BIOLOGICAL EXAMPLES

This Example illustrates the pesticidal/insecticidal properties of compounds of formula (I). The tests were performed as follows:

*Spodoptera littoralis* (Egyptian Cotton Leafworm)

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT).

The following compounds gave at least 80% control of *Spodoptera littoralis*:
A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, A36, A37, A38, A39, A40, A41, A42, A43, A44, A45, A46, A47, A48, A49, A50, A51, A52, A53, A54, A55, A56, A57, A58, A59, A60, B1, B2, B3, B4, B5, B6, B7, B8, B9, B10, B11, B12, B13, B14, B15, B16, B17, B18, B19, B20, B21, B22, B23, B24, B25, B26, C1, C2, C3, C4, C5, C6, C7, C8, C9, C10, C11, C12, C13, C14, C15, C16, C17, D1, D2, D3, D4, D5, E1, E2, E4, E5, E6, E7, E8, E9, E10, F1, F2.

*Heliothis virescens* (Tobacco Budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.

The following compounds gave at least 80% control of *Heliothis virescens*:
A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, A36, A37, A38, A39, A40, A41, A42, A43, A44, A45, A46, A47, A48, A49, A50, A51, A52, A53, A54, A55, A56, A57, A58, A59, A60, B1, B2, B3, B4, B5, B6, B7, B8, B9, B10, B11, B12, B13, B14, B15, B16, B17, B18, B19, B20, B21, B22, B23, B24, B25, B26, C1, C2, C3, C4, C5, C6, C7, C8, C9, C10, C11, C12, C13, C14, C15, C16, C17, D1, D2, D3, D4, D5, E1, E2, E4, E5, E6, E7, E8, E9, E10, F1, F2.

*Plutella xylostella* (Diamond Back Moth):

24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.

The following compounds gave at least 80% control of *Plutella xylostella*:
A1, A2, A3, A4, A5, A6, A7, A8, A9, A10, A11, A12, A13, A14, A15, A16, A17, A18, A19, A20, A21, A22, A23, A25, A26, A27, A28, A29, A30, A31, A32, A33, A34, A35, A36, A37, A38, A39, A40, A41, A42, A43, A44, A45, A46, A47, A48, A49, A50, A51, A52, A53, A54, A55, A56, A57, A58, A59, A60, B1, B2, B3, B4, B5, B6, B7, B8, B9, B10, B11, B12, B13, B14, B15, B16, B17, B18, B19, B20, B21, B22, B23, B24, B25, B26, C1, C2, C3, C4, C5, C6, C7, C8, C9, C10, C11, C12, C13, C14, C15, C16, C17, D1, D2, D3, D4, D5, E1, E2, E4, E5, E6, E7, E8, E9, E10, F1, F2.

*Diabrotica balteata* (Corn Root Worm):

A 24-well microtiter plate (MTP) with artificial diet was treated with test solutions at an application rate of 200 ppm (concentration in well 18 ppm) by pipetting. After drying, the MTP's were infested with larvae (L2) (6-10 per well). After an incubation period of 5 days, samples were checked for larval mortality, and growth regulation.

The following compounds gave at least 80% control of *Diabrotica balteata*:
A1, A2, A3, A4, A5, A6, A7, A8, A9, A10, A11, A12, A13, A14, A15, A16, A17, A18, A19, A20, A21, A22, A23, A24, A25, A27, A28, A30, A32, A33, A34, A35, A37, A38, A39, A40, A41, A42, A43, A44, A45, A46, A47, A48, A49, A52, A53, A54, A55, A56, A57, A58, A59, A60, B1, B2, B3, B4, B5, B6, B7, B8, B9, B10, B11, B12, B13, B14, B15, B16, B17, B18, B19, B20, B21, B22, B23, B24, B25, B26, C1, C2, C3, C4, C5, C6, C7, C8, C9, C10, C11, C12, C17, D1, D2, D3, D4, D5, E1, E2, E4, E5, E6, E7, E8, E9, E10, F1, F2.

The invention claimed is:
1. A compound of formula (I):

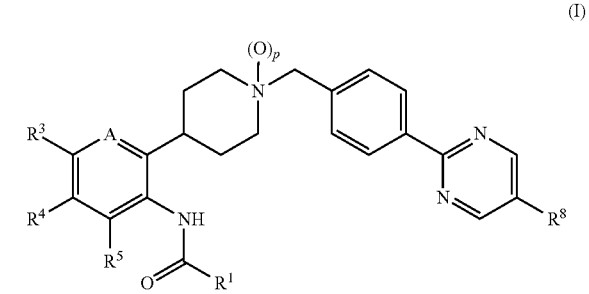

wherein
A is CR$^2$ or N;
p is 0 or 1;

$R^1$ is pyrid-4-yl optionally substituted by one or two substituents each independently selected from halogen, $C_1$-$C_3$alkyl, $C_1$-$C_3$haloalkyl, or $C_1$-$C_3$alkoxy;

$R^2$ is hydrogen, halogen, $C_1$-$C_3$haloalkyl or $C_1$-$C_3$haloalkoxy;

$R^3$ and $R^4$ are independently hydrogen, halogen, cyano, $C_1$-$C_8$alkyl, $C_1$-$C_8$haloalkyl, $C_2$-$C_8$alkenyl, $C_2$-$C_8$haloalkenyl, $C_3$-$C_8$cycloalkyl, $C_3$-$C_8$halocycloalkyl, $C_1$-$C_8$alkoxy, $C_1$-$C_8$haloalkoxy, $C_1$-$C_8$alkylthio or $C_1$-$C_8$haloalkylthio;

$R^5$ is hydrogen or halogen; and $R^8$ is hydrogen, halogen, cyano, $C_1$-$C_8$alkyl, $C_1$-$C_8$haloalkyl, $C_3$-$C_8$cycloalkyl, $C_2$-$C_8$alkenyl, $C_2$-$C_8$haloalkenyl, $C_2$-$C_8$alkynyl, $C_1$-$C_8$alkoxy or $C_1$-$C_8$haloalkoxy; or a salt thereof.

2. A compound according to claim 1 wherein $R^1$ is pyrid-4-yl optionally substituted by one or two substituents each independently selected from fluoro, chloro, bromo, methyl, difluoromethyl, chlorodifluoromethyl, trifluoromethyl or methoxy.

3. A compound according to claim 1 wherein $R^3$ is hydrogen, halogen, cyano, $C_1$-$C_6$alkyl, $C_1$-$C_6$haloalkyl, $C_2$-$C_6$alkenyl, $C_3$-$C_6$cycloalkyl, $C_1$-$C_6$alkoxy, $C_1$-$C_6$haloalkoxy, $C_1$-$C_6$alkylthio or $C_1$-$C_6$haloalkylthio.

4. A compound according to claim 1 wherein $R^4$ is hydrogen, halogen, cyano, $C_1$-$C_6$alkyl, $C_1$-$C_6$haloalkyl, $C_2$-$C_6$alkenyl, $C_3$-$C_6$cycloalkyl, $C_1$-$C_6$alkoxy, $C_1$-$C_6$haloalkoxy, $C_1$-$C_6$alkylthio or $C_1$-$C_6$haloalkylthio.

5. A compound according to claim 1 wherein $R^5$ is hydrogen, fluoro, chloro or bromo.

6. A compound according to claim 1 wherein $R^8$ is hydrogen, halogen, cyano, $C_1$-$C_6$alkyl, $C_1$-$C_6$haloalkyl, $C_3$-$C_6$cycloalkyl, $C_2$-$C_6$alkenyl, $C_2$-$C_6$haloalkenyl, $C_2$-$C_6$alkynyl, $C_1$-$C_6$alkoxy or $C_1$-$C_6$haloalkoxy.

7. A method of combating and controlling insects which comprises applying to a pest, to a locus of a pest, or to a plant susceptible to attack by a pest an insecticidally effective amount of a compound of formula (I) as defined in claim 1.

8. An insecticidal composition comprising an insecticidally effective amount of a compound of formula (I) as defined in claim 1.

* * * * *